United States Patent
Maruo et al.

(10) Patent No.: US 7,154,737 B2
(45) Date of Patent: Dec. 26, 2006

(54) NONAQUEOUS ELECTROLYTE, ELECTRICAL DOUBLE-LAYER CAPACITORS, AND NONAQUEOUS ELECTROLYTE SECONDARY CELLS

(75) Inventors: Tatsuya Maruo, Chiba (JP); Shoko Marukane, Chiba (JP); Gen Masuda, Chiba (JP); Takaya Sato, Chiba (JP)

(73) Assignee: Nisshinbo Industries, Inc., Tokyo (JP)

( * ) Notice: Subject to any disclaimer, the term of this patent is extended or adjusted under 35 U.S.C. 154(b) by 0 days.

(21) Appl. No.: 10/528,053

(22) PCT Filed: Sep. 19, 2003

(86) PCT No.: PCT/JP03/11978

§ 371 (c)(1), (2), (4) Date: Mar. 17, 2005

(87) PCT Pub. No.: WO2004/027788

PCT Pub. Date: Apr. 1, 2004

(65) Prior Publication Data

US 2006/0034035 A1    Feb. 16, 2006

(30) Foreign Application Priority Data

Sep. 20, 2002    (JP)    ............... 2002-274348

(51) Int. Cl.
*H01G 9/00*    (2006.01)
*H01G 9/02*    (2006.01)

(52) U.S. Cl. ............. 361/502; 361/503; 361/525; 252/62.2

(58) Field of Classification Search ........ 361/503–505, 361/525–527; 252/62.2
See application file for complete search history.

(56) References Cited

U.S. PATENT DOCUMENTS

| | | | |
|---|---|---|---|
| 5,454,980 A | 10/1995 | Schlueter et al. | |
| 6,841,299 B1* | 1/2005 | Wariishi | 429/188 |
| 2005/0231894 A1* | 10/2005 | Yoshida et al. | 361/502 |
| 2006/0035137 A1* | 2/2006 | Maruo et al. | 429/46 |

FOREIGN PATENT DOCUMENTS

| | | |
|---|---|---|
| EP | 0 657 896 A1 | 6/1995 |
| EP | 1 075 005 A2 | 2/2001 |
| EP | 1 089 305 A2 | 4/2001 |
| EP | 1 380 569 A1 | 1/2004 |
| EP | 1 498 409 A1 | 1/2005 |
| EP | 1 548 866 A1 | 6/2005 |
| JP | 6-220147 A | 8/1994 |
| JP | 7-238219 A | 9/1995 |
| JP | 8-245828 A | 9/1996 |
| JP | 10-265673 A | 10/1998 |
| JP | 10-265674 A | 10/1998 |
| JP | 11-86905 A | 3/1999 |
| JP | 2001-167630 A | 6/2001 |
| JP | 2001-256828 A | 9/2001 |
| JP | 2003-86470 A | 3/2003 |

* cited by examiner

*Primary Examiner*—Eric W. Thomas
(74) *Attorney, Agent, or Firm*—Birch, Stewart, Kolasch & Birch, LLP

(57) ABSTRACT

Secondary cells and electrical double-layer capacitors of excellent charge-discharge efficiency, stability and low-temperature properties can be obtained using nonaqueous electrolytes which contain an ionic liquid that has general formula (1) below and is liquid at not higher than 50° C. and an ion-conductive polymer.

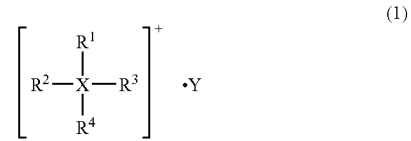

In formula (1), $R^1$ to $R^4$ are each independently an alkyl group of 1 to 5 carbons or an alkoxyalkyl group of the formula $R'—O—(CH_2)_n—$ ($R'$ being methyl or ethyl, and the letter $n$ being an integer from 1 to 4), and any two from among $R^1$, $R^2$, $R^3$ and $R^4$ may together form a ring, with the proviso that at least one of $R^1$ to $R^4$ is an alkoxyalkyl group of the above formula. X is a nitrogen atom or a phosphorus atom, and Y is a monovalent anion.

17 Claims, No Drawings

NONAQUEOUS ELECTROLYTE, ELECTRICAL DOUBLE-LAYER CAPACITORS, AND NONAQUEOUS ELECTROLYTE SECONDARY CELLS

TECHNICAL FIELD

The present invention relates to nonaqueous electrolytes, and to electrical double-layer capacitors and nonaqueous electrolyte secondary cells in which such nonaqueous electrolytes are used.

BACKGROUND ART

Ionic compounds generally exist in the form of crystals composed of positively charged cations and negatively charged anions which pull electrostatically on each other. Such ionic compounds dissolve in water and various other liquids to form liquids that conduct electricity, i.e., electrolyte solutions.

Some ionic compounds maintain a liquid state at room temperature and do not solidify even at very low temperatures. Such ionic compounds which maintain a liquid state at room temperature or below are referred to in particular as "room-temperature fused salts" or "ionic liquids." To minimize electrostatic interactions between the cations and anions which make up the ionic liquid, either the cations or anions or both are molecular ions of a significant size. Moreover, to minimize the charge and electrostatic interactions, either or both are monovalent.

Active research efforts are being made to employ such ionic liquids as electrolytes in batteries and other applications. However, in general, ionic liquids have a high hydroscopic property and are difficult to handle in air. As a result, their use has remained limited.

In light of these circumstances, the 1-ethyl-3-methylimidazolium tetrafluoroborate reported by Wilkes et al. in 1992 is a remarkable ionic liquid that can be handled even in air. This new ionic liquid led to the synthesis of many ionic liquids which are combinations of numerous alkylimidazolium cations having different side chains with various anions.

Such developments have gradually led to efforts to use ionic liquids as electrolytes in nonaqueous electrolyte secondary cells. For example, JP-A 8-245828 (Patent Reference 1), JP-A 10-265673 (Patent Reference 2) and JP-A 10-265674 (Patent Reference 3) disclose solid electrolytes which use polymeric compound complexes containing a room-temperature fused salt (ionic liquid) and a polymeric compound (and lithium salt). Solid electrolytes which employ such polymeric compound complexes are able to reduce the tendency for leakage associated with the use of liquid electrolytes.

Each of the foregoing patent references mentions the use of substances such as cyclic amidine onium salts, pyridine onium salts and aliphatic quaternary ammonium salts of organic carboxylic acids as room-temperature fused salts. However, because these room-temperature fused salts do not have very broad potential windows, they are readily subject to reductive decomposition during charging and discharging of the electrochemical devices such as secondary cells and tend to degrade, thus lacking a performance adequate for practical use.

Also, these room-temperature fused salts have relatively high solidification points, and thus remain inadequate in terms of increasing the low-temperature properties of electrochemical devices such as secondary cells.

Moreover, in the above-described electrolytes which employ a polymeric compound complex, because the polymer itself either lacks ionic conductivity or has only a poor ionic conductivity, the polymer complex obtained with the polymer has a greatly diminished ionic conductivity.

In light of these circumstances, one object of the present invention is to provide nonaqueous electrolytes which contain an ionic liquid and a polymeric compound and afford electrical double-layer capacitors and nonaqueous electrolyte secondary cells having excellent charge-discharge efficiency, stability and low-temperature characteristics. Additional objects of the invention are to provide electrical double-layer capacitors and nonaqueous electrolyte secondary cells in which such nonaqueous electrolytes are used.

DISCLOSURE OF THE INVENTION

The inventors have conducted extensive investigations in order to achieve the above objects. As a result, they have found that quaternary ammonium salts and quaternary phosphonium salts bearing at least one alkoxyalkyl group as a substituent have the properties of ionic liquids. Moreover, the inventors have found that because these ionic liquids exhibit a liquid state even at low temperatures and have a broad potential window, they are not readily subject to reductive decomposition during the charging and discharging of a battery, for example. In addition, the inventors have learned that by using nonaqueous electrolytes containing such an ionic liquid and an ion-conductive polymeric compound as the nonaqueous electrolyte in electrical double-layer capacitors and nonaqueous electrolyte secondary cells, there can be obtained electrical double-layer capacitors and nonaqueous electrolyte secondary cells endowed with excellent charge-discharge efficiency and excellent stability and low-temperature characteristics. These discoveries led ultimately to the present invention.

Accordingly, the invention provides the following:

(1) A nonaqueous electrolyte characterized by containing an ionic liquid which has general formula (1) below and is liquid at not higher than 50° C.

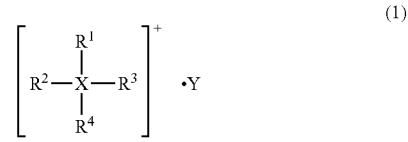

wherein $R^1$ to $R^4$ are each independently an alkyl group of 1 to 5 carbons or an alkoxyalkyl group of the formula $R'-O-(CH_2)_n-$ ($R'$ being methyl or ethyl, and the letter n being an integer from 1 to 4), and any two from among $R^1$, $R^2$, R3 and $R^4$ may together form a ring, with the proviso that at least one of $R^1$ to $R^4$ is an alkoxyalkyl group of the above formula, X is a nitrogen atom or a phosphorus atom, and Y is a monovalent anion; and containing also an ion-conductive polymer.

(2) A nonaqueous electrolyte which is characterized in that it is obtained by curing a composition containing an ionic liquid which has general formula (1) below and is liquid at not higher than 50° C.

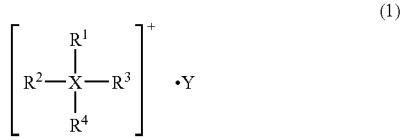

wherein $R^1$ to $R^4$ are each independently an alkyl group of 1 to 5 carbons or an alkoxyalkyl group of the formula $R'—O—(CH_2)_n—$ ($R'$ being methyl or ethyl, and the letter n being an integer from 1 to 4), and any two from among $R^1$, $R^2$, $R^3$ and $R^4$ may together form a ring, with the proviso that at least one of $R^1$ to $R^4$ is an alkoxyalkyl group of the above formula, X is a nitrogen atom or a phosphorus atom, and Y is a monovalent anion; and containing also a compound having a reactive double bond on the molecule, and an ion-conductive polymer.

(3) The nonaqueous electrolyte of (1) or (2) above which is characterized by containing a lithium salt.

(4) The nonaqueous electrolyte of (3) above which is characterized in that the lithium salt is $LiBF_4$, $LiPF_6$, $Li(CF_3SO_2)_2N$, $LiCF_3SO_3$ or $LiCF_3CO_2$.

(5) The nonaqueous electrolyte of any one of (1) to (4) above which is characterized in that the ion-conductive polymer is a noncrystalline polymer.

(6) The nonaqueous electrolyte of any one of (1) to (5) above which is characterized in that the ion-conductive polymer has a relative permittivity at 25° C. and 1 MHz of 5 to 50.

(7) The nonaqueous electrolyte of any one of (1) to (6) above which is characterized in that the ion-conductive polymer is a thermoplastic polyurethane resin.

(8) The nonaqueous electrolyte of any one of (1) to (6) above which is characterized in that the ion-conductive polymer is a hydroxyalkyl polysaccharide or a hydroxyalkyl polysaccharide derivative.

(9) The nonaqueous electrolyte of any one of (1) to (6) above which is characterized in that the ion-conductive polymer is a polymeric compound having an average degree of polymerization of at least 20 and containing polyvinyl alcohol units of general formula (2) below

wherein n is a number from 20 to 10,000, some or all of the hydroxyl groups on the polyvinyl alcohol units being substituted with oxyalkylene-bearing groups having an average molar substitution of at least 0.3.

(10) The nonaqueous electrolyte of any one of (1) to (6) above which is characterized in that the ion-conductive polymer is a polymeric compound having an average degree of polymerization of at least 20 and containing polyvinyl alcohol units of general formula (2) below

wherein n is a number from 20 to 10,000, some or all of the hydroxyl groups on the polyvinyl alcohol units being substituted with cyano-substituted monovalent hydrocarbon groups.

(11) The nonaqueous electrolyte of any one of (1) to (6) above which is characterized in that the ion-conductive polymer is a polymeric compound having units of formula (3) and units of formula (4)

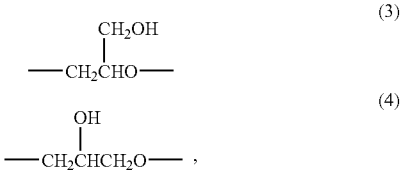

wherein at least 10% of the end groups on the molecular chain are capped with one or more groups selected from among halogen atoms, substituted or unsubstituted monovalent hydrocarbon groups, $R^5CO—$ groups ($R^5$ being a substituted or unsubstituted monovalent hydrocarbon group), $R^5{}_3Si—$ groups ($R^5$ being the same as above), amino groups, alkylamino groups, $H(OR^6)_m—$ groups ($R^6$ being an alkylene group of 2 to 4 carbons, and m being an integer from 1 to 100) and phosphorus atom-containing groups.

(12) The nonaqueous electrolyte of any one of (1) to (11) above which is characterized in that the ionic liquid is liquid at not higher than 25° C.

(13) The nonaqueous electrolyte of any one of (1) to (12) above which is characterized in that X is a nitrogen atom, R' is methyl, and n is 2.

(14) The nonaqueous electrolyte of any one of (1) to (12) above which is characterized in that the ionic liquid has general formula (5) below

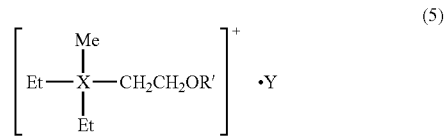

wherein R' is methyl or ethyl, X is a nitrogen atom or a phosphorus atom, Y is a monovalent anion, Me stands for methyl and Et stands for ethyl.

(15) The nonaqueous electrolyte of any one of (1) to (14) above which is characterized in that Y is $BF_4{}^-$, $PF_6{}^-$, $(CF_3SO_2)_2N^-$, $CF_3SO_3{}^-$ or $CF_3CO_2{}^-$.

(16) An electrical double-layer capacitor comprising a pair of polarizable electrodes, a separator between the polarizable electrodes and a nonaqueous electrolyte; which electrical double-layer capacitor is characterized in that the nonaqueous electrolyte is a nonaqueous electrolyte according to any one of (1) to (15) above.

(17) A nonaqueous electrolyte secondary cell comprising a positive electrode which contains a lithium-containing double oxide, a negative electrode which contains a carbonaceous material capable of lithium ions insertion and extraction or contains metallic lithium, a separator between the positive and negative electrodes, and a nonaqueous electrolyte; which nonaqueous secondary cell is characterized in that the nonaqueous electrolyte is a nonaqueous electrolyte according to any one of (1) to (15) above.

Because the nonaqueous electrolyte of the invention contains an ionic liquid that exhibits a liquid state even at low temperatures and has a broad potential window and contains also an ion-conductive polymer, it has an excellent ionic conductivity, stability and other properties. By using this nonaqueous electrolyte as the electrolyte in secondary cells and electrical double-layer capacitors, there can be obtained secondary cells and capacitors having an excellent charge-discharge efficiency and having excellent stability, cycle retention and low-temperature characteristics.

BEST MODE FOR CARRYING OUT THE INVENTION

The invention is described more fully below.

[Nonaqueous Electrolyte]

The ionic liquid used in the nonaqueous electrolyte according to the invention has general formula (1) below and is in a liquid state at not higher than 50° C.

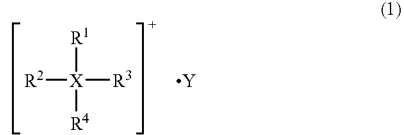

(1)

In formula (1), $R^1$ to $R^4$ are each independently an alkyl group of 1 to 5 carbons or an alkoxyalkyl group of the formula $R'$—O—$(CH_2)_n$— (R' being methyl or ethyl, and the letter n being an integer from 1 to 4), and any two from among $R^1$, $R^2$, $R^3$ and $R^4$ may together form a ring, with the proviso that at least one of $R^1$ to $R^4$ is an alkoxyalkyl group of the above formula. X is a nitrogen atom or a phosphorus atom, and Y is a monovalent anion.

Examples of alkyls having 1 to 5 carbons include methyl, ethyl, propyl, 2-propyl, butyl and pentyl. However, taking into account the physical properties and the electrochemical characteristics of the ionic liquid, it is preferable for at least one of groups $R^1$ to $R^4$ to be methyl, ethyl or propyl, and especially methyl or ethyl. These ethyl or propyl groups may form rings with other alkyl groups.

Examples of alkoxyalkyl groups of the formula R'—O—$(CH_2)_n$— include methoxymethyl, ethoxymethyl, methoxyethyl, ethoxyethyl, methoxypropyl, ethoxypropyl, methoxybutyl and ethoxybutyl. The letter n is an integer from 1 to 4. However, taking into account the physical properties and the electrochemical characteristics of the ionic liquid, the letter n is preferably 1 or 2, and most preferably 2.

Exemplary compounds in which any two groups from among $R^1$ to $R^4$ form a ring include, when X is a nitrogen atom, quaternary ammonium salts containing an aziridine, azetidine, pyrrolidine or piperidine ring; and, when X is a phosphorus atom, quaternary phosphonium salts containing a pentamethylenephosphine (phosphorinane) ring.

Quaternary ammonium salts having as a substituent at least one methoxyethyl group, in which R' above is methyl and the letter n is 2, are preferred.

Preferred use can also be made of quaternary salts of general formula (5) below having as substituents a methyl group, two ethyl groups and an alkoxyethyl group, and compounds of general formula (6) below having as substituents two methyl groups, an ethyl group and an alkoxyethyl group.

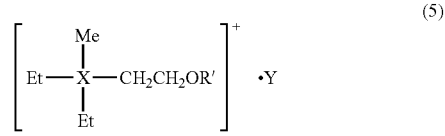

(5)

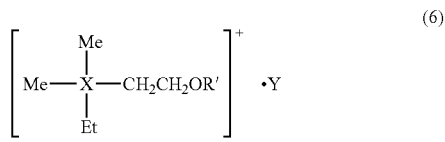

(6)

In formulas (5) and (6), R' is methyl or ethyl, X is a nitrogen or phosphorus atom, and Y is a monovalent anion. Me represents a methyl group and Et represents an ethyl group.

Illustrative, non-limiting examples of the monovalent anion Y include $BF_4^-$, $PF_6^-$, $AsF_6^-$, $SbF_6^-$, $AlCl_4^-$, $HSO_4^-$, $ClO_4^-$, $CH_3SO_3^-$, $CF_3SO_3^-$, $CF_3CO_2^-$, $(CF_3SO_2)_2N^-$, $Cl^-$, $Br^-$ and $I^-$. To ensure such properties as a good degree of dissociation and good stability, the use of $BF_4^-$, $PF_6^-$, $(CF_3SO_2)_2N^-$, $CF_3SO_3^-$ or $CF_3CO_2^-$ is preferred.

Of these anions, the use of $(CF_3SO_2)_2N^-$ is highly preferable for further reducing the viscosity of the ionic liquid and increasing its handleability. $BF_4^-$ is also highly preferable because the resulting ionic liquid has a high versatility and is less readily affected by water than ionic liquids containing $PF_6^-$ as the anion and thus easier to handle.

Specific examples of ionic liquids highly suitable for use in the invention include compounds (7) to (19) below (wherein "Me" stands for methyl and "Et" stands for ethyl).

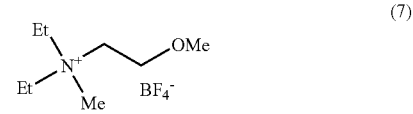

(7)

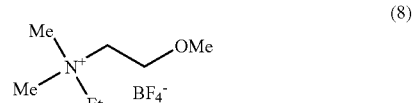

(8)

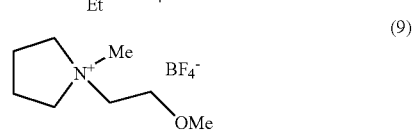

(9)

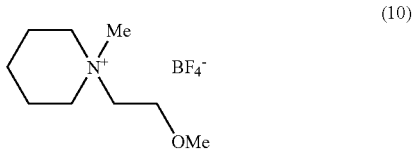

(10)

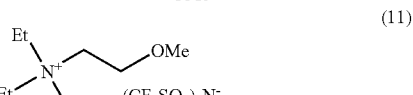

(11)

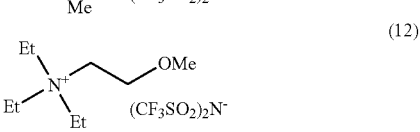

(12)

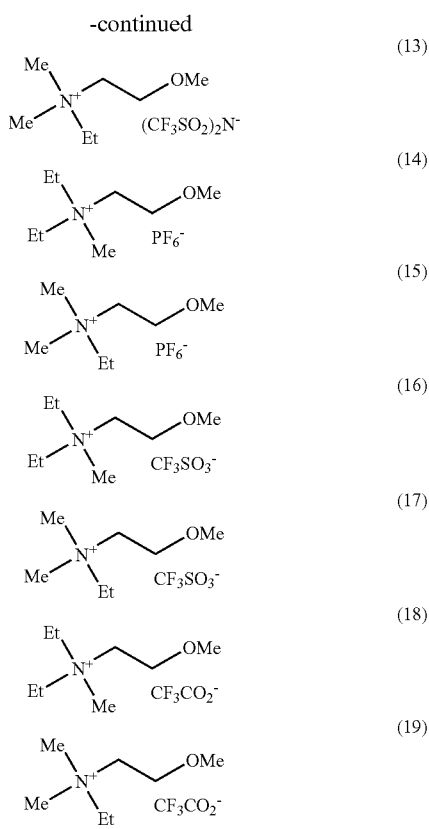

A common method for synthesizing such quaternary ammonium salts is described. First, a tertiary amine is mixed with a compound such as an alkyl halide or a dialkyl sulfate and reacted under heating, if necessary, to give a quaternary ammonium halide. In cases where a compound having a low reactivity (e.g., an alkoxyethyl halide or an alkoxymethyl halide) is used, reaction under applied pressure, such as in an autoclave, is desirable.

The resulting quaternary ammonium halide is dissolved in an aqueous solvent such as water, then reacted with a reagent that generates the required anionic species, such as tetrafluoroboric acid or tetrafluorophosphoric acid, so as to effect an anion exchange reaction, yielding the quaternary ammonium salt.

In one illustrative method for synthesizing quaternary ammonium tetrafluoroborate, a quaternary ammonium halide is dissolved in water, silver oxide is added and a salt exchange reaction is carried out to form the corresponding quaternary ammonium hydroxide. The product is then reacted with tetrafluoroboric acid, yielding the target compound. This method is effective for synthesizing high-purity quaternary ammonium tetrafluoroborates because the silver halide that arises as a result of salt exchange during formation of the quaternary ammonium hydroxide can easily be removed.

Quaternary phosphonium salts can generally be synthesized in much the same way as quaternary ammonium salts. Typically, a tertiary phosphine is mixed with a suitable compound such as an alkyl halide or a dialkyl sulfate. If necessary, the reaction is carried out under the application of heat.

As in the case of quaternary ammonium salts, quaternary phosphonium salts containing various different anions may be prepared by dissolving a quaternary phosphonium halide (a chloride, bromide or iodide) in an aqueous solvent and reacting the dissolved halide with a reagent that generates the required anionic species so as to effect an anion exchange reaction.

The above ionic liquid is in a liquid state at a temperature not higher than 50° C., preferably not higher than 25° C., and most preferably not higher than 15° C. Because nonaqueous electrolyte secondary cells and electrical double-layer capacitors are normally used at temperatures of from 50° C. down to −10° C., there is no point in using an ionic liquid which is not in a liquid state within this temperature range. The lower the temperature at which the ionic liquid is in a liquid state, the more desirable because this broadens the temperature range in which the nonaqueous electrolyte secondary cell and the electrical double-layer capacitor can be used.

Because the ionic liquid of the invention is in a liquid state at a lower temperature than the imidazolium ion-containing ionic liquids which have hitherto been used, by employing a nonaqueous electrolyte containing this ionic liquid as the electrolyte in a nonaqueous electrolyte secondary cell or an electrical double-layer capacitor, secondary cells and electrical double-layer capacitors having even better low-temperature characteristics can be obtained.

Also, because the ionic liquid has a broad potential window and is not itself readily subject to reductive decomposition during charging and discharging, there can be obtained an electrolyte which resists deterioration even when charging and discharging are repeatedly carried out. As a result, highly stable secondary cells and electrical double-layer capacitors can be achieved.

The first nonaqueous electrolyte according to the invention contains the above-described ionic liquid and an ion-conductive polymer.

The ion-conductive polymer here is not subject to any particular limitation, although to manifest a high ionic conductivity it is preferable for this polymer to be non-crystalline.

Also, in general, cation and anion dissociation is strongly promoted within a highly polar matrix. Accordingly, the ionic conductivity can be substantially increased by a method involving mixture with a highly polar polymer. From this standpoint, it is preferable to use as the ion-conductive polymer a polymer having a relative permittivity at 25° C. and 1 MHz of from 5 to 50, and especially from 10 to 50. To increase the polarity of the polymer matrix, it is desirable to introduce substituents having a large dipole moment onto the polymer. One preferred example of such substituents is the cyano group.

Ion-conductive polymers having all the above characteristics that are preferable for use include (a) hydroxyalkyl polysaccharide derivatives, (b) oxyalkylene branched polyvinyl alcohol derivatives, (c) polyglycidol derivatives, (d) cyano-substituted monovalent hydrocarbon group-bearing polyvinyl alcohol derivatives, and (e) thermoplastic polyurethane resins.

Illustrative examples of (a) hydroxyalkyl polysaccharide derivatives include: (1) hydroxyethyl polysaccharides prepared by reacting ethylene oxide with a naturally occurring polysaccharide such as cellulose, starch or pullulan; (2) hydroxypropyl polysaccharides prepared by reacting propylene oxide with the above naturally occurring polysaccharides; and (3) dihydroxypropyl polysaccharides prepared by reacting glycidol or 3-chloro-1,2-propanediol with the above naturally occurring polysaccharides. Hydroxyalkyl polysaccharide derivatives in which some or all of the hydroxyl groups on these hydroxyalkyl polysaccharides are capped with an ester-bonded or ether-bonded substituent are preferred.

The above hydroxyalkyl polysaccharides have a molar substitution of 2 to 30, and preferably 2 to 20. At the molar substitution of less than 2, the salt dissolving ability of the hydroxyalkyl polysaccharide may become so low as to make it unsuitable for use.

Oxyalkylene branched polyvinyl alcohol derivatives (b) suitable for use as the polymeric compound include polymeric compounds which bear on the molecule polyvinyl alcohol units of general formula (2) below, which have an average degree of polymerization of at least 20, and in which some or all of the hydroxyl groups on the polyvinyl alcohol units are substituted with oxyalkylene-bearing groups having an average molar substitution of at least 0.3.

In formula (2), the letter n is preferably from 20 to 10,000.

Because this type of polymeric compound has a high oxyalkylene fraction, it has the ability to dissolve a large amount of salt. In addition, the molecule contains many oxyalkylene segments which permit the movement of ions, resulting in a high ion mobility. This type of polymeric compound is thus capable of exhibiting a high ionic conductivity. Moreover, these polymeric compounds have a high tackiness. Accordingly, they act as a binder component and are capable of firmly bonding the positive and negative electrodes.

Examples of polymeric compounds of above formula (2) include [1] polymeric compounds obtained by reacting a polyvinyl alcohol unit-containing polymeric compound with an oxirane compound such as ethylene oxide, propylene oxide or glycidol (e.g., dihydroxypropylated polyethylene vinyl alcohol, propylene oxide-modified polyvinyl alcohol); and [2] polymeric compounds obtained by reacting a polymeric compound having polyvinyl alcohol units with a polyoxyalkylene compound having terminal hydroxy-reactive substituents.

Here, the polyvinyl alcohol unit-bearing polymeric compound is a polymeric compound which has polyvinyl alcohol units on the molecule, which has a number-average degree of polymerization of at least 20, preferably at least 30, and most preferably at least 50, and in which some or all of the hydroxyl groups on the polyvinyl alcohol units are substituted with oxyalkylene-bearing groups. For the sake of handleability, the upper limit in the number-average degree of polymerization in this case is preferably not more than 2,000, more preferably not more than 500, and most preferably not more than 200.

It is most preferable for the above-described polyvinyl alcohol unit-bearing polymeric compound to have a number-average degree of polymerization within the above range and to be a homopolymer in which the fraction of polyvinyl alcohol units in the molecule is at least 98 mol %. However, the polyvinyl alcohol unit-bearing polymeric compound is not limited to the above, and may be one which has a number-average degree of polymerization within the above range and which has a polyvinyl alcohol fraction of preferably at least 60 mol %, and more preferably at least 70 mol %. Illustrative examples of such compounds that may be used include polyvinyl formals in which some of the hydroxyl groups on the polyvinyl alcohol have been converted to formal, modified polyvinyl alcohols in which some of the hydroxyl groups on the polyvinyl alcohol have been converted to alkyls, poly(ethylene vinyl alcohols), partially saponified polyvinyl acetates, and other modified polyvinyl alcohols.

This polymeric compound is one in which some or all of the hydroxyl groups on the above-described polyvinyl alcohol units are substituted with oxyalkylene-containing groups having an average molar substitution of at least 0.3 (moreover, some of the hydrogen atoms on these oxyalkylene groups may be substituted with hydroxyl groups). Preferably at least 30 mol %, and most preferably at least 50 mol %, of the hydroxyl groups are substituted in this way.

The above-mentioned polyglycidol derivative (c) contains units of formula (3) (referred to hereinafter as "A units")

and units of formula (4) (referred to hereinafter as "B units")

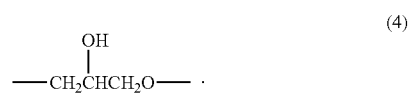

The ends of the molecular chain are capped with specific substituents.

The polyglycidol can be prepared by polymerizing glycidol or 3-chloro-1,2-propanediol, although it is generally preferable to carry out polymerization from glycidol as the starting material and using a basic catalyst or a Lewis acid catalyst.

The total number of A and B units on the polyglycidol molecule is at least two, preferably at least six, and most preferably at least ten. There is no particular upper limit, although it is generally preferable for the total number of such units to not exceed about 10,000. The total number of these respective units may be set as appropriate based on such considerations as the flow ability and viscosity required of the polyglycidol. The ratio of A units to B units in the molecule, expressed as A/B, is within a range of 1/9 to 9/1, and preferably 3/7 to 7/3. There is no regularity to the arrangement of A and B units; any combination is possible The polyglycidol has a polyethylene glycol equivalent weight-average molecular weight (Mw), as determined by gel permeation chromatography (GPC), within a range of preferably 200 to 730,000, more preferably 200 to 100,000, and most preferably 600 to 20,000. The dispersity, defined as weight-average molecular weight divided by number-average molecular weight (Mw/Mn) is preferably 1.1 to 20, and most preferably 1.1 to 10.

These polymeric compounds (a) to (c) may be hydroxyl-capped polymer derivatives in which some or all, and preferably at least 10 mol %, of the hydroxyl groups on the molecule are capped with one or more type of monovalent substituent selected from among halogen atoms, substituted or unsubstituted monovalent hydrocarbon groups having 1 to 10 carbons, $R^5CO-$ groups (wherein $R^5$ is a substituted or unsubstituted monovalent hydrocarbon group of 1 to 10 carbons), $R^5_3Si$— groups (wherein $R^5$ is as defined above), amino groups, alkylamino groups and phosphorus atom-containing groups.

Illustrative examples of the substituted or unsubstituted monovalent hydrocarbon groups having 1 to 10 carbons include alkyl groups such as methyl, ethyl, propyl, isopropyl, t-butyl and pentyl, aryl groups such as phenyl and tolyl, aralkyl groups such as benzyl, alkenyl groups such as vinyl, and any of the foregoing in which some or all of the hydrogen atoms have been substituted with halogen atoms, cyano groups, hydroxyl groups or amino groups. Any one or combination of two or more of these types of groups may be used.

Capping the hydroxyl groups on the above polymeric compounds (a) to (c) with highly polar substituents increases the polarity (and thus the relative permittivity) of the polymer matrix, making it possible to prevent the decline in conductivity which readily arises in a low relative permittivity polymer matrix due to the recombination of dissociated cations and counteranions. Moreover, when capping is done using substituents that have fire-retarding and hydrophobic properties, the polymeric compound can be imparted with desirable characteristics such as hydrophobicity and fire retardance.

To increase the relative permittivity of above polymeric compounds (a) to (c), the oxyalkylene chain-bearing polymeric compounds (a) to (c) are reacted with a hydroxy-reactive compound so as to cap the hydroxyl groups on these polymeric compounds with highly polar substituents.

Although the highly polar substituents used for this purpose are not subject to any particular limitation, neutral substituents are preferable to ionic substituents. Exemplary substituents include substituted and unsubstituted monovalent hydrocarbon groups of 1 to 10 carbons, and $R^5CO$— groups (wherein $R^5$ is as defined above). If necessary, capping may also be carried out with other suitable substituents, such as amino groups or alkylamino groups.

To confer polymeric compounds (a) to (c) with hydrophobic properties and fire retardance, the hydroxyl groups on the above polymeric compounds may be capped with, for example, halogen atoms, $R^5_3Si$— groups (wherein $R^5$ is as defined above) or phosphorus-containing groups.

Examples of suitable $R^5_3Si$— groups include those in which $R^5$ represents the same substituted or unsubstituted monovalent hydrocarbon groups having 1 to 10 carbons, and preferably 1 to 6 carbons, as above. $R^5$ preferably stands for alkyl groups. Trialkylsilyl groups, and especially trimethylsilyl groups, are preferred.

Additional examples of suitable substituents include amino groups, alkylamino groups and phosphorus atom-containing groups.

The proportion of end groups capped with the above substituents is at least 10 mol %, preferably at least 50 mol %, and most preferably at least 90 mol %. It is even possible to cap substantially all the end groups with the above substituents, representing a capping ratio of about 100 mol %.

The above-mentioned cyano-substituted monovalent hydrocarbon group-bearing polyvinyl alcohol derivative (d) is preferably a polymeric compound which bears on the molecule polyvinyl alcohol units of above general formula (2), which has an average degree of polymerization of at least 20, and in which some or all of the hydroxyl groups on the polyvinyl alcohol units are substituted with cyano-substituted monovalent hydrocarbon groups.

Because this polymeric compound has relatively short side chains, the viscosity of the electrolyte can be held to a low level.

Examples of such polymeric compounds include polyvinyl alcohols in which some or all of the hydroxyl groups have been substituted with groups such as cyanoethyl, cyanobenzyl or cyanobenzoyl. Cyanoethyl-substituted polyvinyl alcohols are especially preferred because the side chains are short.

Various known methods may be used to substitute the hydroxyl groups on the polyvinyl alcohol with cyano-substituted monovalent hydrocarbon groups.

The above-mentioned thermoplastic polyurethane resin (e) is preferably a thermoplastic polyurethane resin prepared by reacting (A) a polyol compound, (B) a polyisocyanate compound and, if necessary, (C) a chain extender.

Suitable thermoplastic polyurethane resins include not only polyurethane resins having urethane bond, but also polyurethane-urea resins having both urethane bond and urea bond.

The polyol compound serving as component A is preferably a polyether polyol, a polyester polyol, a polyester polyether polyol, a polyester polycarbonate polyol, a polycaprolactone polyol, or a mixture thereof.

The polyol compound serving as component A has a number-average molecular weight of preferably 1,000 to 5,000, and most preferably 1,500 to 3,000. A polyol compound having too small a number-average molecular weight may lower the physical properties of the resulting thermoplastic polyurethane resin film, such as the heat resistance and tensile elongation percentage. On the other hand, too large a number-average molecular weight increases the viscosity during synthesis, which may lower the production stability of the thermoplastic polyurethane resin being prepared. The number-average molecular weights used here in connection with polyol compounds are calculated based on the hydroxyl values measured in accordance with JIS K1577.

Illustrative examples of the polyisocyanate compound serving as component B include aromatic diisocyanates such as tolylene diisocyanate, 4,4'-diphenylmethane diisocyanate, p-phenylene diisocyanate, 1,5-naphthylene diisocyanate and xylylene diisocyanate; and aliphatic or alicyclic diisocyanates such as hexamethylene diisocyanate, isophorone diisocyanate, 4,4'-dicyclohexylmethane diisocyanate and hydrogenated xylylene diisocyanate.

The chain extender serving as component C is preferably a low-molecular-weight compound having a molecular weight of not more than 300 and bearing two active hydrogen atoms capable of reacting with isocyanate groups.

Various known compounds may be used as such low-molecular-weight compounds. Illustrative examples include aliphatic diols such as ethylene glycol, propylene glycol and 1,3-propanediol; aromatic or alicyclic diols such as 1,4-bis (β-hydroxyethoxy)benzene, 1,4-cyclohexanediol and bis (βhydroxyethyl) terephthalate; diamines such as hydrazine, ethylenediamine, hexamethylenediamine and xylylenediamine; and amino alcohols such as adipoyl hydrazide. Any one or combinations of two or more of these may be used.

The thermoplastic polyurethane resin typically includes 5 to 200 parts by weight, and preferably 20 to 100 parts by weight, of the polyisocyanate compound serving as component B and 1 to 200 parts by weight, and preferably 5 to 100 parts by weight, of the chain extender serving as component C per 100 parts by weight of the polyol compound serving as component A.

A lithium salt can also be added to the first nonaqueous electrolyte described above. The lithium salt employed for this purpose may be any known lithium salt capable of being used in nonaqueous electrolyte secondary cells. To ensure such properties as versatility and both good solubility and a high degree of dissociation in the ionic liquid, the use of $LiBF_4$, $LiPF_6$, $Li(CF_3SO_2)_2N$, $LiCF_3SO_3$ or $LiCF_3CO_2$ is especially preferred.

The content of lithium salt in the above electrolyte is not subject to any particular limitation, although the content is generally 0.05 to 3 mol/L, and preferably 0.1 to 2 mol/L. Too low a lithium salt concentration may result in a higher cell impedance, which make charging and discharging at a large current impossible. On the other hand, a lithium salt concentration which is too high increases the liquid viscosity, which may make battery and capacitor production difficult.

In addition, if necessary, the above-described electrolyte may have added thereto cyclic or acylic esters, cyclic carboxylates, cyclic or acyclic ethers, phosphates, lactone compounds, nitrile compounds, amide compounds, and mixtures thereof.

Exemplary cyclic carbonates include alkylene carbonates such as propylene carbonate (PC), ethylene carbonate (EC) and butylene carbonate; and vinylene carbonate (VC). Exemplary acyclic carbonates include dialkyl carbonates such as dimethyl carbonate (DMC), methyl ethyl carbonate (MEC) and diethyl carbonate (DEC). Exemplary acyclic carboxylates include methyl acetate and methyl propionate. Exemplary cyclic and acyclic ethers include tetrahydrofuran, 1,3-dioxolane and 1,2-dimethoxyethane. Exemplary phosphates include trimethyl phosphate, triethyl phosphate, ethyldimethyl phosphate, diethylmethyl phosphate, tripropyl phosphate, tributyl phosphate, tri(trifluoromethyl) phosphate, tri(trichloromethyl) phosphate, tri(trifluoroethyl) phosphate, tri(triperfluoroethyl) phosphate, 2-ethoxy-1,3,2-dioxaphosphoran-2-one, 2-trifluoroethoxy-1,3,2-dioxaphosphoran-2-one and 2-methoxyethoxy-1,3,2-dioxaphosphoran-2-one. An example of a suitable lactone compound is γ-butyrolactone. An example of a suitable nitrile compound is acetonitrile. An example of a suitable amide compound is dimethylformamide. Of these compounds, cyclic carbonates, phosphates, and mixtures thereof are preferred.

As explained above, the nonaqueous electrolyte of the invention, because it includes a specific ionic liquid, can provide nonaqueous electrolyte secondary cells and electrical double-layer capacitors which undergo little deterioration of cyclability and thus have an excellent stability, and which have excellent low-temperature characteristics.

Moreover, because this nonaqueous electrolyte has a broader potential window than ionic liquids known to the prior art, the ionic liquid itself does not readily undergo reductive decomposition during charging and discharging. As a result, the cycle retention and stability of electrochemical devices such as nonaqueous electrolyte secondary cells which use this electrolyte can be improved. Also, because the above ionic liquid exhibits a liquid state at lower temperatures than prior-art ionic liquids, nonaqueous electrolytes having better low-temperature characteristics can be obtained.

Furthermore, because the above nonaqueous electrolyte includes the above-described conductive polymeric compound, it can manifest a high ionic conductivity, in addition to which it can act as a binder component and is fully capable of firmly bonding together the positive and negative electrodes.

The second nonaqueous electrolyte of the invention is obtained by curing a composition containing the above-described ionic liquid and ion-conductive polymer, and containing also a compound having a reactive double bond on the molecule. In this invention, curing is a concept which encompasses also gelation.

That is, in cases where the nonaqueous electrolyte obtained by curing or gelating the above composition is formed into a thin film and used as the electrolyte in a secondary cell or capacitor, to increase the physical strength (e.g., shape retention), a compound having a reactive double bond on the molecule and an ion-conductive polymer are added, and the compound is reacted to form a polymer.

It is particularly desirable for the compound bearing a reactive double bond on the molecule to have two or more reactive double bonds, because the reaction of such a compound forms a three-dimensional network structure, making it possible to increase even further the shape retaining ability of the electrolyte.

When the nonaqueous electrolyte of the invention includes not only the above-mentioned compound having at least two reactive double bonds, but also the above-described conductive polymeric compound, there can be obtained an electrolyte having a semi-interpenetrating polymer network (semi-IPN) structure in which the molecular chains of the polymeric compound are intertwined with the three-dimensional network structure of the polymer formed by crosslinkage of the reactive double bond-bearing compound. The shape retention and strength of the electrolyte can thus be further increased, and its adhesive properties and ion conductivity also enhanced.

The second nonaqueous electrolyte may also include within the composition the same lithium salt as that described above in connection with the first nonaqueous electrolyte. The amount of such lithium salt included may be set within the same range as described above for the first nonaqueous electrolyte.

Likewise, ion-conductive polymers that may be used in the second nonaqueous electrolyte are of the same type as those described above in connection with the first nonaqueous electrolyte. The amount of ion-conductive polymer included is not subject to any particular limitation, although it is preferable for the weight ratio (ion-conductive polymer/reactive double bond-containing compound) to be set within a range of 0.001 to 0.1, and especially 0.003 to 0.005.

In addition, if necessary, the same cyclic or acyclic esters, acyclic carboxylates, cyclic or acyclic ethers, phosphates, lactone compounds, nitrile compounds, amide compounds or mixtures thereof as described above in connection with the first nonaqueous electrolyte may also be included.

The compound having a reactive double bond on the molecule is not subject to any particular limitation. Illustrative examples include acrylates and methacrylates such as glycidyl methacrylate, glycidyl acrylate, methoxydiethylene glycol methacrylate, methoxytriethylene glycol methacrylate and methoxypolyethylene glycol methacrylate (average molecular weight, 200 to 1,200); and other compounds having one acrylic acid group or methacrylic acid group on the molecule, such as methacryloyl isocyanate, 2-hydroxymethylmethacrylic acid and N,N-dimethylaminoethylmethacrylic acid.

In cases where a semi-IPN structure is to be formed using such a compound having a single reactive double bond and the ion-conductive polymeric compound described above, it is necessary to add also a compound having at least two reactive double bonds on the molecule.

Preferred examples of the compound having two or more reactive double bonds on the molecule include divinylbenzene, divinylsulfone, allyl methacrylate, ethylene glycol dimethacrylate, diethylene glycol dimethacrylate, triethylene glycol dimethacrylate, polyethylene glycol dimethacrylate (average molecular weight, 200 to 1,000), 1,3-butylene glycol dimethacrylate, 1,6-hexanediol dimethacrylate, neopentyl glycol dimethacrylate, polypropylene glycol dimethacrylate (average molecular weight, 400), 2-hydroxy-1,3-dimethacryloxypropane, 2,2-bis [4-(methacryloxyethoxy)phenyl]propane, 2,2-bis [4-(methacryloxyethoxy-diethoxy)phenyl]propane, 2,2-bis [4-(methacryloxyethoxy-polyethoxy)phenyl]propane, ethylene glycol diacrylate, diethylene glycol diacrylate, triethylene glycol diacrylate, polyethylene glycol diacrylate (average molecular weight, 200 to 1,000), 1,3-butylene glycol diacrylate, 1,6-hexanediol diacrylate, neopentyl glycol diacrylate, polypropylene glycol diacrylate (average molecular weight, 400), 2-hydroxy-1,3-diacryloxypropane, 2,2-bis [4-(acryloxyethoxy)phenyl] propane, 2,2-bis [4-(acryloxyethoxy-diethoxy)phenyl] propane, 2,2-bis [4-(acryloxyethoxy-polyethoxy)phenyl] propane, trimethylolpropane triacrylate, trimethylolpropane trimethacrylate, tetramethylolmethane triacrylate, tetramethylolmethane tetraacrylate, water-soluble urethane diacrylate, water-soluble urethane dimethacrylate, tricyclodecane dimethanol acrylate, hydrogenated dicyclopentadiene diacrylate, polyester diacrylate and polyester dimethacrylate.

Of the aforementioned reactive double bond-bearing compounds, especially preferred reactive monomers include the polyoxyalkylene component-bearing diesters of general formula (15) below. The use of such a diester in combination with a polyoxyalkylene component-bearing monoester of general formula (16) below and a triester is recommended.

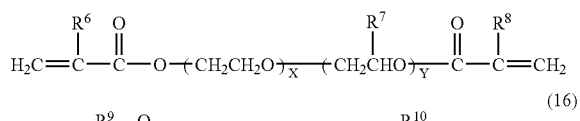

(15)

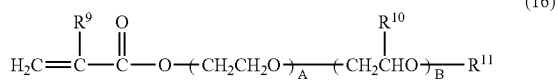

(16)

In formula (15), $R^6$ to $R^8$ are each independently a hydrogen atom or an alkyl group having 1 to 6 carbons, and preferably 1 to 4 carbons, such as methyl, ethyl, n-propyl, i-propyl, n-butyl, i-butyl, s-butyl or t-butyl; and X and Y satisfy the condition $X \geq 1$ and $Y \geq 0$ or the condition $X \geq 0$ and $Y \geq 1$. $R^6$ to $R^8$ are preferably methyl, ethyl, n-propyl, i-propyl, n-butyl, i-butyl, s-butyl or t-butyl.

In formula (16), $R^9$ to $R^{11}$ are each independently a hydrogen atom or an alkyl group having 1 to 6 carbons, and preferably 1 to 4 carbons, such as methyl, ethyl, n-propyl, i-propyl, n-butyl, i-butyl, s-butyl or t-butyl; and A and B satisfy the condition $A \geq 1$ and $B \geq 0$ or the condition $A \geq 0$ and $B \geq 2$. $R^9$ to $R^{11}$ are preferably methyl, ethyl, n-propyl, i-propyl, n-butyl, i-butyl, s-butyl or t-butyl.

A preferred example of the compound of above formula (15) is one in which X is 9, Y is 0, and both $R^6$ and $R^8$ are $CH_3$. A preferred example of the compound of above formula (16) is one in which A is 2 or 9, B is 0, and both $R^9$ and $R^{11}$ are $CH_3$.

The triester is preferably trimethylolpropane trimethacrylate.

The above-described polyoxyalkylene component-bearing diester and polyoxyalkylene component-bearing monoester are exposed, in a mixture together with the above-described ionic liquid and polymeric compound, to a suitable form of radiation (e.g., UV light, electron beams, x-rays, gamma rays, microwaves, radio-frequency radiation). Alternatively, the mixture is heated to form a semi-IPN-type three-dimensional crosslinked network structure.

The relative proportions of the above-described polyoxyalkylene component-bearing diester, monoester and triester are set as appropriate for the length of the polyoxyalkylene components and are not subject to any particular limitation. However, a diester/monoester molar ratio of 0.1 to 2, and especially 0.3 to 1.5, and a diester/triester molar ratio of 2 to 15, and especially 3 to 10, are preferred to enhance the strength of the electrolyte.

As explained above, the polymer electrolyte obtained by curing (gelating) a composition containing the nonaqueous electrolyte of the invention and a reactive double bond-containing compound, in addition to having the above-mentioned properties such as low-temperature characteristics, cyclability, ionic conductivity and tackiness, also has a high shape-retaining ability.

In particular, because the electrolyte obtained by curing a composition which includes a compound bearing at least two reactive double bonds as the compound having a reactive double bond on the molecule and which contains also the above-described polymeric compound has a semi-IPN type three-dimensional crosslinked network structure, the shape retaining ability and strength of the electrolyte can be increased all the more, as can also its adhesive properties and ionic conductivity.

[Electrical Double-Layer Capacitor]

The electrical double-layer capacitor according to this invention is an electrical double-layer capacitor having a pair of polarizable electrodes, a separator between the polarizable electrodes, and the above-described nonaqueous electrolyte.

The polarizable electrodes used here may be ones obtained by coating a current collector with a polarizable electrode composition containing a carbonaceous material and a binder polymer.

The carbonaceous material is not subject to any particular limitation. Illustrative examples include carbonaceous materials prepared by the carbonization of a suitable starting material, or by both carbonization and subsequent activation of the carbonized material to yield activated carbon. Examples of suitable starting materials include plant-based materials such as wood, sawdust, coconut shells and pulp spent liquor; fossil fuel-based materials such as coal and petroleum fuel oil, as well as fibers spun from coal or petroleum pitch obtained by the thermal cracking of such fossil fuel-based materials or from tar pitch; and synthetic polymers, phenolic resins, furan resins, polyvinyl chloride resins, polyvinylidene chloride resins, polyimide resins, polyamide resins, polycarbodiimide resins, liquid-crystal polymers, plastic waste and reclaimed tire rubber.

The method of activation is not subject to any particular limitation. Any of various methods, such as chemical activation and steam activation, may be used. However, activated carbons prepared by chemical activation using potassium hydroxide are especially preferred because they tend to provide a larger capacitance than steam-activated product.

The carbonaceous material used in the invention may be in any of various forms, including shredded material, granulated material, pellets, fibers, felt, woven fabric or sheet.

A conductive material may be added to the carbonaceous material. The conductive material may be any suitable material capable of conferring electrical conductivity to the carbonaceous material. Illustrative, non-limiting, examples include carbon black, Ketjenblack, acetylene black, carbon whiskers, carbon fibers, natural graphite, artificial graphite, titanium oxide, ruthenium oxide, and metallic fibers such as those made of aluminum and nickel. Any one or combinations of two or more thereof may be used. Of these, Ketjenblack and acetylene black, which are both types of carbon black, are preferred.

The average particle size of the conductive material, though not subject to any particular limitation, is preferably 10 nm to 10 μm, more preferably 10 to 100 nm, and even more preferably 20 to 40 nm. It is especially advantageous for the conductive material to have an average particle size which is from 1/5000 to 1/2, and preferably from 1/1000 to 1/10, the average particle size of the carbonaceous material.

The amount of conductive material added is not subject to any particular limitation, although an amount of from 0.1 to 20 parts by weight, and preferably 0.5 to 10 parts by weight, per 100 parts by weight of the carbonaceous material is desirable for achieving a good electrostatic capacitance and imparting electrical conductivity.

The binder polymer mentioned above may be any polymer capable of being used in the applications of concern here. For example, use can be made of various known binder polymers, such as polytetrafluoroethylene, polyvinylidene fluoride, carboxymethyl cellulose, fluoroolefin copolymer-type crosslinked polymers, polyvinyl alcohol, polyacrylic acid, polyimide, petroleum pitch, coal pitch and phenolic resins.

It is especially preferred to use as the binder polymer (I) a thermoplastic resin having a swelling ratio, as defined by the formula below, in a range of 150 to 800%, (II) a fluoropolymer material, or a combination of two or more polymers of types (I) and (II).

The above thermoplastic resin (I) has a swelling ratio, as determined from the formula indicated below, within a range of 150 to 800%, preferably 250 to 500%, and most preferably 250 to 400%.

$$\text{Swelling ratio (\%)} = \frac{\text{Weight in grams of swollen thermoplastic resin after 24 hours immersion in electrolyte solution at 20° C. (g)}}{\text{Weight in grams of thermoplastic resin before immersion in electrolyte solution at 20° C. (g)}} \times 100$$

A thermoplastic resin containing units of general formula (17) below

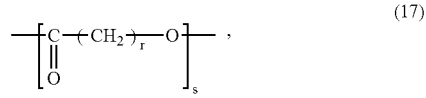

(17)

wherein the letter r is 3 to 5 and the letter s is an integer ≧5, may be used as the binder polymer of formula (I) above.

Preferred examples of fluoropolymer materials (II) that may be used as the binder polymer include polyvinylidene fluoride (PVDF), vinylidene fluoride-hexafluoropropylene copolymers (P(VDF-HFP)) and vinylidene fluoride-chlorotrifluoroethylene copolymers (P(VDF-CTFE)). Of these, fluoropolymers having a vinylidene fluoride content of at least 50 wt %, and especially at least 70 wt %, are preferred.

The upper limit in the vinylidene fluoride content of the fluoropolymer is about 97 wt %.

The weight-average molecular weight of the fluoropolymer is not subject to any particular limitation, although the weight-average molecular weight is preferably 500,000 to 2,000,000, and most preferably 500,000 to 1,500,000. Too low a weight-average molecular weight may result in an excessive decline in physical strength.

It is preferable for these binder polymers to be added in an amount of 0.5 to 20 parts by weight, and especially 1 to 10 parts by weight, per 100 parts by weight of the carbonaceous material.

No particular limitation is imposed on the method of preparing the polarizable electrode composition. For example, the composition may be prepared by rendering the above-described carbonaceous material and binder polymer into the form of a solution. If necessary, a solvent may be added to this solution.

The resulting polarizable electrode composition is applied onto a current collector to form a polarizable electrode. The method of application is not subject to any particular limitation. Any known method of application, such as one involving the use of a doctor blade or an air knife, may be suitably employed.

The current collectors used for this purpose may be any positive and negative electrode current collectors commonly employed in electrical double-layer capacitors. The positive electrode current collector is preferably aluminum foil or aluminum oxide, and the negative electrode current collector is preferably copper foil, nickel foil, or a metal foil covered on the surface with a copper plating film or a nickel plating film.

The foils making up the respective current collectors may be in any of various shapes, including thin foils, flat sheets, and perforated, stampable sheets. The foil has a thickness of generally about 1 to 200 μm. Taking into account such characteristics as the density of the activated carbon as a portion of the overall electrode and the electrode strength, a thickness of 8 to 100 μm, and especially 8 to 30 μm, is preferred.

Alternatively, the polarizable electrodes can be produced by melting and blending the polarizable electrode composition, then extruding the blend as a film.

A conductive material may be added to the above-described activated carbon. The conductive material may be any suitable material capable of conferring electrical conductivity to the activated carbon. Illustrative, non-limiting, examples include carbon black, Ketjenblack, acetylene black, carbon whiskers, carbon fibers, natural graphite, artificial graphite, titanium oxide, ruthenium oxide, and metallic fibers such as those made of aluminum and nickel. Any one or combinations of two or more thereof may be used. Of these, Ketjenblack and acetylene black, which are both types of carbon black, are preferred.

The average particle size of the conductive material, though not subject to any particular limitation, is preferably 10 nm to 10 μm, more preferably 10 to 100 nm, and even more preferably 20 to 40 nm. It is especially advantageous for the conductive material to have an average particle size which is from 1/5000 to 1/2, and preferably from 1/1000 to 1/10, the average particle size of the activated carbon.

The amount of conductive material added is not subject to any particular limitation, although an amount of from 0.1 to 20 parts by weight, and preferably 0.5 to 10 parts by weight, per 100 parts by weight of the activated carbon is desirable for achieving a good electrostatic capacitance and imparting electrical conductivity.

The separator may be one that is commonly used in electrical double-layer capacitors. Illustrative examples include polyolefin nonwoven fabric, polytetrafluoroethylene porous film, kraft paper, sheet laid from a blend of rayon fibers and sisal fibers, manila hemp sheet, glass fiber sheet, cellulose-based electrolytic paper, paper made from rayon fibers, paper made from a blend of cellulose and glass fibers, and combinations thereof in the form of multilayer sheets.

The electrical double-layer capacitor of the invention can be assembled by stacking, fan-folding or winding an electrical double-layer capacitor assembly composed of the above-described pair of polarizable electrodes with a separator therebetween. The capacitor assembly is then placed within a capacitor housing such as a can or a laminate pack, following which the housing is filled with electrolyte or a polymer electrolyte-forming composition then mechanically sealed if it is a can or heat-sealed if it is a laminate pack. When a polymer electrolyte-forming composition is used, this may then be reacted to effect curing.

The resulting electrical double-layer capacitor of the invention can be operated at a high capacity and a high current without comprising such desirable characteristics as its excellent charge-discharge efficiency, high energy density, high power density and long life. Moreover, it has a broad service temperature range.

The electrical double-layer capacitors of the invention are highly suitable for use as a memory backup power supply for cell phones, notebook computers and portable remote terminals, as a power supply for cell phones and portable acoustic devices, as an uninterruptible power supply for personal computers and other equipment, and as various types of low-current electrical storage devices such as load leveling power supplies used in combination with solar power generation and wind power generation. Moreover, electrical double-layer capacitors capable of being charged and discharged at a high current are suitable for use as high-current electrical storage devices in applications that require a large current, such as electric cars and electrical power tools.

[Secondary Cells]

The secondary cell according to this invention is a secondary cell having a positive electrode which contains a lithium-containing double oxide, a negative electrode containing a carbonaceous material capable of lithium ion insertion and extraction or containing metallic lithium, a separator between the positive and negative electrodes, and which is the above-described nonaqueous electrolyte.

The positive electrode may be one that is produced by coating both the front and back sides or just one side of a positive electrode current collector with a positive electrode binder composition composed primarily of a binder polymer and a positive electrode active material.

Alternatively, a positive electrode binder composition composed primarily of a binder polymer and a positive electrode active material may be melted and blended, then extruded as a film to form the positive electrode.

The binder polymer may be any polymer capable of being used in the applications of concern here, such as the binder polymers described above in connection with electrical double-layer capacitors.

The positive electrode current collector may be made of a suitable material such as stainless steel, aluminum, titanium, tantalum or nickel. Of these, aluminum foil or aluminum oxide foil is especially preferred both in terms of performance and cost. This current collector may be used in any of various forms, including foil, expanded metal, sheet, foam, wool, or a three-dimensional structure such as a net.

In this invention, lithium ion-containing chalcogen compounds (lithium-containing double oxides) may be used as the above positive electrode active material.

Specific examples of such lithium ion-containing chalcogen compounds (lithium-containing double oxides) include $LiCoO_2$, $LiMnO_2$, $LiMn_2O_4$, $LiMo_2O_4$, $LiV_3O_8$, $LiNiO_2$ and $Li_xNi_yM_{1-y}O_2$ (wherein M is one or more metal element selected from among cobalt, manganese, titanium, chromium, vanadium, aluminum, tin, lead and zinc; $0.05 \leq x \leq 1.10$; and $0.5 \leq y \leq 1.0$).

In addition to the binder resin and the positive electrode active material described above, if necessary, the binder composition for the positive electrode may include also an electrically conductive material. Illustrative examples of the conductive material include carbon black, Ketjenblack, acetylene black, carbon whiskers, carbon fibers, natural graphite and artificial graphite.

The positive electrode binder composition typically includes 1,000 to 5,000 parts by weight, and preferably 1,200 to 3,500 parts by weight, of the positive electrode active material and 20 to 500 parts by weight, and preferably 50 to 400 parts by weight, of the conductive material per 100 parts by weight of the binder polymer.

The negative electrode may be a negative electrode composed of lithium metal or a negative electrode produced by coating both the front and back sides or just one side of a negative electrode current collector with a negative electrode binder composition composed primarily of a binder polymer and a negative electrode active material. The same binder polymer may be used as in the positive electrode.

Alternatively, the negative electrode binder composition composed primarily of a binder polymer and a negative electrode active material may be melted and blended, then extruded as a film to form a negative electrode.

The negative electrode current collector may be made of a suitable material such as copper, stainless steel, titanium or nickel. Of these, copper foil or a metal foil whose surface is covered with a copper plating film is especially preferred both in terms of performance and cost. The current collector used may be in any of various forms, including foil, expanded metal, sheet, foam, wool, or a three-dimensional structure such as a net.

The negative electrode active material may be, for example, an alkali metal, an alkali metal alloy, an oxide, sulfide or nitride of at least one element selected from among group 8, 9, 10, 11, 12, 13, 14 and 15 elements of the periodic table, which oxide, sulfide or nitride is capable of lithium ion insertion and extraction, or a carbonaceous material capable of reversible lithium ion insertion and extraction.

Examples of suitable alkali metals include lithium, sodium and potassium. Examples of suitable alkali metal alloys include metallic lithium, Li—Al, Li—Mg, Li—Al—Ni, sodium, Na—Hg and Na—Zn.

Illustrative examples of the oxides of at least one element selected from periodic table group 8 to 15 elements capable of lithium ion insertion and extraction include tin silicon oxide ($SnSiO_3$), lithium bismuth oxide ($Li_3BiO_4$) and lithium zinc oxide ($Li_2ZnO_2$).

Illustrative examples of the sulfides include lithium iron sulfides $Li_xFeS_2$ (wherein $0 \leq x \leq 3$) and lithium copper sulfides $Li_xCuS$ (wherein $0 \leq x \leq 3$).

Illustrative examples of the nitrides include lithium-containing transition metal nitrides, and specifically $Li_xM_yN$ (wherein M is cobalt, nickel or copper; $0 \leq x \leq 3$; and $0 \leq y \leq 0.5$) and lithium iron nitride ($Li_3FeN_4$).

Examples of carbonaceous materials which are capable of reversible lithium ion insertion and extraction include lo graphite, carbon black, coke, glassy carbon, carbon fibers, and sintered bodies obtained from any of these.

If necessary, a conductive material may be added to the negative electrode binder composition as well. Examples of suitable conductive materials include the same materials as those mentioned above in connection with the positive electrode binder.

The negative electrode binder composition typically includes 500 to 1,700 parts by weight, preferably 700 to 1,300 parts by weight, of the negative electrode active material and 0 to 70 parts by weight, preferably 0 to 40 parts by weight, of the conductive material per 100 parts by weight of the binder polymer.

The above-described negative electrode binder compositions and positive electrode binder compositions generally are used in the form of a paste after the addition of a dispersing medium. Suitable dispersing media include polar solvents such as N-methyl-2-pyrrolidone (NMP), dimethylformamide, dimethylacetamide and dimethylsulfamide. The dispersing medium is typically added in an amount of about 30 to 300 parts by weight per 100 parts by weight of the positive electrode or negative electrode binder composition.

No particular limitation is imposed on the method of shaping the positive and negative electrodes as thin films, although it is preferable to apply the composition by a suitable means such as roller coating with an applicator roll, screen coating, doctor blade coating, spin coating or bar coating so as to form an active material layer having a uniform thickness when dry of 10 to 200 μm, and especially 50 to 150 μm.

Illustrative, non-limiting, examples of the separator between the positive and negative electrodes include polyethylene nonwoven fabric, polypropylene nonwoven fabric, polyester nonwoven fabric, polytetrafluoroethylene porous film, kraft paper, sheet laid from a blend of rayon fibers and sisal fibers, manila hemp sheet, glass fiber sheet, cellulose-based electrolytic paper, paper made from rayon fibers, paper made from a blend of cellulose and glass fibers, and combinations thereof in the form of multilayer sheets.

The secondary cell of the invention is assembled by stacking, fan-folding, winding or forming into a laminated or coin-like shape a cell assembly composed of the separator disposed between the positive and negative electrodes, and placing the cell assembly within a battery housing such as a battery can or a laminate pack. The battery housing is mechanically sealed if it is a can or heat-sealed if it is a laminate pack. In constructing the cell, the separator is disposed between the positive electrode and the negative electrode, the resulting cell assembly is placed within the battery housing, then the cell assembly is filled with nonaqueous electrolyte. If a compound having reactive double bonds is used as the nonaqueous electrolyte, the electrolyte composition is filled into the cell assembly so that it fully penetrates the gap between the electrodes and the gaps between the separator and the electrodes, then is reacted to effect curing.

The resulting nonaqueous electrolyte secondary cell of the invention can be operated at a high capacity and a high current without compromising such desirable characteristics as its excellent charge-discharge efficiency, high energy density, high output density and long life. Moreover, the cell has a broad service temperature range.

The nonaqueous electrolyte secondary cell of the invention lends itself well to use in a variety of applications, including main power supplies and memory backup power supplies for portable electronic equipment such as video cameras, notebook computers, cell phones and PHS ("personal handyphone system") devices, uninterruptible power supplies for equipment such as personal computers, in electric cars and hybrid cars, and together with solar cells as energy storage systems for solar power generation.

EXAMPLE

The following synthesis examples, examples of the invention and comparative examples are provided to illustrate the invention and do not in any way limit the invention.

Synthesis Example 1

Synthesis of Compound (6)

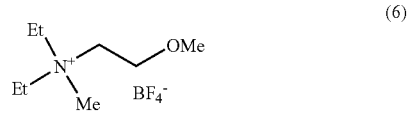

(6)

A solution prepared by mixing together 100 mL of diethylamine (Kanto Chemical Co., Inc.) and 85 mL of 2-methoxyethyl chloride (Kanto Chemical) was placed in an autoclave and reacted at 100° C. for 24 hours. The internal pressure during the reaction was 0.127 MPa (1.3 kgf/cm$^2$). This yielded a mixture of deposited crystals and reaction solution to which was added, following the 24 hours of reaction, 200 mL of an aqueous solution containing 56 g of dissolved potassium hydroxide (Katayama Chemical Industries Co., Ltd.). Each of the two divided organic phases that formed as a result was separated off with a separatory funnel and subjected twice to extraction with 100 mL of methylene chloride (Wako Pure Chemical Industries, Ltd.). The separated organic phases were then combined and washed with a saturated saline solution, following which potassium carbonate (Wako Pure Chemical Industries) was added to remove water and vacuum filtration was carried out. The solvent in the resulting organic phase was distilled off in a rotary evaporator, after which the residue was subjected to normal-pressure distillation, yielding 18.9 g of a fraction having a boiling point close to 135° C. This was confirmed from a $^1$H-NMR spectrum to be 2-methoxyethyldiethylamine.

Next, 8.24 g of the 2-methoxyethyldiethylamine was dissolved in 10 mL of tetrahydrofuran (Wako Pure Chemical Industries), then 4.0 mL of methyl iodide (Wako Pure Chemical Industries) was added under ice cooling. After 30 minutes, the mixture was removed from the ice bath and stirred overnight at room temperature. The solvent in this reaction solution was subsequently driven off by vacuum distillation, and the resulting solids were recrystallized from an ethanol (Wako Pure Chemical Industries)—tetrahydrofuran system, yielding 16 g of 2-methoxyethyldiethylmethylammonium iodide.

Next, 15.0 g of the 2-methoxyethyldiethylmethyl ammonium iodide was dissolved in 100 mL of distilled water, after which 6.37 g of silver oxide (Kanto Chemical) was added and the mixture was stirred for 3 hours. This reaction mixture was vacuum filtered to remove precipitates, following which 42% tetrafluoroboric acid (Kanto Chemical) was added a little at a time under stirring until the reaction solution reached a pH of about 5 to 6. This reaction solution was then freeze-dried and water was thoroughly driven off with a vacuum pump, yielding 12.39 g of compound (6) which was liquid at room temperature (25° C.).

Synthesis Example 2

Synthesis of Compound (11)

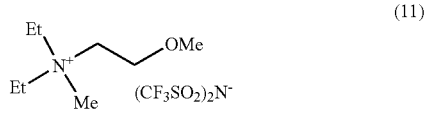
(11)

2-Methoxyethyldiethylmethylammonium iodide (10.0 g) obtained by the same method as in Synthesis Example 1 was dissolved in 50 mL of acetonitrile (Kanto Chemical), following which 9.5 g of lithium bis(trifluoromethanesulfonyl) imide (produced by Kishida Chemical Co., Ltd.) was added and completely dissolved therein, and the resulting solution was stirred for 15 minutes.

The acetonitrile was removed by vacuum distillation, following which water was added to the residue, causing the organic phase to divide into two. The organic phases were then separated off and washed five times with water to remove impurities.

The washed organic phases were subsequently placed under reduced pressure with a vacuum pump and the water was thoroughly driven off, yielding 6.8 g of compound (11), which was liquid at room temperature.

Synthesis Example 3

Synthesis of Thermoplastic Polyurethane Resin

A reactor equipped with a stirrer, a thermometer and a condensing tube was charged with 60.20 parts by weight of a preheated and dehydrated polyethylene glycol 4000 (PEG 4000-S, made by Sanyo Chemical Industries, Ltd.) and 7.84 parts by weight of 4,4'-diphenylmethane diisocyanate. The reactor contents were stirred and mixed for 2 hours at 120° C. under a stream of nitrogen, following which 1.86 parts by weight of 1,4-butanediol was added to the mixture and the reaction was similarly effected at 120° C. under a stream of nitrogen. When the reaction reached the point where the reaction product became rubbery, it was stopped. The reaction product was then removed from the reactor and heated at 100° C. for 12 hours. Once the isocyanate peak was confirmed to have disappeared from the infrared absorption spectrum, heating was stopped, yielding a solid polyurethane resin.

The resulting polyurethane resin had a weight-average molecular weight (Mw) of $1.05 \times 10^5$.

Synthesis Example 4

Synthesis of Cellulose Derivative

Eight grams of hydroxypropyl cellulose (molar substitution, 4.65; product of Nippon Soda Co., Ltd.) was suspended in 400 mL of acrylonitrile, following which 1 mL of 4 wt % aqueous sodium hydroxide was added and the mixture was stirred 4 hours at 30° C. The reaction mixture was then neutralized with acetic acid and poured into a large amount of methanol, giving cyanoethylated hydroxypropyl cellulose.

To remove impurities, the cyanoethylated hydroxypropyl cellulose was dissolved in acetone, following which the solution was placed in a dialysis membrane tube and purified by dialysis using ion-exchanged water. The cyanoethylated hydroxypropyl cellulose which settled out during dialysis was collected and dried.

Elemental analysis of the resulting cyanoethylated hydroxypropyl cellulose indicated a nitrogen content of 7.3 wt %. Based on this value, the proportion of the hydroxyl groups on the hydroxypropyl cellulose that were capped with cyanoethyl groups was 94%.

Synthesis Example 5

Synthesis of Oxyalkylene-Branched Polyvinyl Alcohol Derivative

A reactor equipped with a stirring element was charged with 10 parts by weight of polyvinyl alcohol (average degree of polymerization, 500; vinyl alcohol fraction, ≧98%) and 70 parts by weight of acetone. A solution of 1.81 parts by weight of sodium hydroxide in 2.5 parts by weight of water was gradually added under stirring, after which stirring was continued for one hour at room temperature. To this solution was gradually added, over a period of 3 hours, a solution of 67 parts by weight of glycidol in 100 parts by weight of acetone. The resulting mixture was stirred for 8 hours at 50° C. to effect the reaction. Following reaction completion, stirring was stopped, whereupon the polymer precipitated from the mixture. The precipitate was collected, dissolved in 400 parts by weight of water, and neutralized with acetic acid. The neutralized polymer was purified by dialysis, and the resulting solution was freeze-dried, giving 22.50 parts by weight of dihydroxypropylated polyvinyl alcohol.

Given that polyvinyl alcohol has a unit molecular weight of 44 and glycidol has a unit molecular weight of 74, a polyvinyl alcohol derivative obtained by the addition of n units of glycidol (molar substitution) would have a unit molecular weight of 44+74n. Such a polyvinyl alcohol derivative would thus have an average molar substitution (MS), as calculated based on this unit molecular weight, the weight of the polyvinyl alcohol charged, and the weight of the product obtained, of n=0.74.

Based on a $^{13}$C-NMR spectrum (DEPT spectrum measured using a Varian VXR-300 NMR spectrometer, with $D_2O$ as the solvent) of this product, the average molar substitution (average MS) determined by comparing the C* carbon signal intensity (A) for —C*H$_2$—C(OH)H— units from the unreacted polyvinyl alcohol with the signal intensity (C) for other carbons was 0.95.

In addition, the fraction of unreacted —(CH$_2$—C(OH) H)— units was determined by comparing the signal intensities (A) and (C). This unreacted fraction a was 0.57.

Accordingly, of the diydroxypropyl groups (DHP) which formed as a result of glycidol addition, the fraction b that reacted was 1−a, or 0.43, and the average length (L) of the DHP chain was L=MS/b=2.21.

Three parts by weight of the resulting polyvinyl alcohol was mixed with 20 parts by weight of dioxane and 14 parts by weight of acrylonitrile. To this mixed solution was added a solution of 0.16 part by weight of sodium hydroxide in 1 part by weight of water, and stirring was carried out for 10 hours at 25° C. The resulting mixture was neutralized using an ion-exchange resin (Amberlite IRC-76, produced by Organo Corporation). The ion-exchange resin was separated off by filtration, after which 50 parts by weight of acetone was added to the solution and the insolubles were filtered off. The resulting acetone solution was placed in dialysis membrane tubing and dialyzed with running water. The polymer which precipitated within the dialysis membrane tubing was collected and re-dissolved in acetone. The resulting solution was filtered, following which the acetone was evaporated off, giving a cyanoethylated polyvinyl alcohol derivative.

The infrared absorption spectrum of this polymer derivative showed no hydroxyl group absorption, confirming that all the hydroxyl groups were capped with cyanoethyl groups (capping ratio, 100%).

Synthesis Example 6

Synthesis of Cyano-Substituted Monovalent Hydrocarbon Group-Bearing Polyvinyl Alcohol Derivative A reaction vessel equipped with a stirring element was charged with 3 parts by weight of polyvinyl alcohol (average degree of polymerization, 500; vinyl alcohol fraction, $\geq 98\%$), 20 parts by weight of 1,4-dioxane and 14 parts by weight of acrylonitrile. To this mixture was gradually added a solution of 0.16 part by weight of sodium hydroxide in 1 part by weight of water, and stirring was carried out for 10 hours at 25° C.

The resulting mixture was neutralized using an ion-exchange resin (Amberlite IRC-76, produced by Organo Corporation). The ion-exchange resin was then separated off by filtration, after which 50 parts by weight of acetone was added to the solution and the insolubles were filtered off. The resulting acetone solution was placed in dialysis membrane tubing and dialyzed with running water. The polymer which precipitated within the dialysis membrane tubing was collected and re-dissolved in acetone. The resulting solution was filtered, following which the acetone was evaporated off, giving a cyanoethylated polyvinyl alcohol derivative.

The infrared absorption spectrum of this polymer derivative showed no hydroxyl group absorption, confirming that all the hydroxyl groups were capped with cyanoethyl groups (capping ratio, 100%).

Example 1

Nonaqueous Electrolyte

[Production of Polyurethane Resin Film]

Five parts by weight of the polyurethane resin obtained in Synthesis Example 3 and 95 parts by weight of N-methyl-2-pyrrolidone were stirred and mixed, giving a polyurethane resin solution. The resulting polyurethane resin solution was applied by means of a doctor blade so as to give a film thickness when dry of 30 μm, then dried in vacuo at 120° C. for 2 hours to give a polyurethane resin film.

[Measurement of Relative Permittivity]

The polyurethane resin film obtained as described above was cut to a size of 4×4 cm, and the relative permittivity of the film at 25° C. and a frequency of 1 MHz was measured using an RF impedance/material analyzer (model 4291B, manufactured by Agilent Technologies, Inc.). The relative permittivity was 16.2.

[Production of Polymer Electrolyte Membrane]

The polyurethane resin film produced as described above was immersed for 24 hours in the ionic liquid prepared in Synthesis Example 1 and thereby impregnated with liquid electrolyte, giving a polymer electrolyte membrane.

[Measurement of Ionic Conductivity]

The resulting polymer electrolyte membrane was placed between two sheets of copper, and the ionic conductivity at 25° C. was measured by the AC impedance method. The ionic conductivity was $2.2 \times 10^{-3}$ S/cm.

[Measurement of Potential Window]

The potential window of the polymer electrolyte membrane produced as described above was measured by potensiostat and function generator using platinum electrodes as the working electrode and the counter electrode, and using a silver/silver chloride electrode as the reference electrode. The polymer electrolyte membrane was thus found to have a potential window with respect to a silver/silver chloride electrode of −3.0 V to +3.0 V.

Comparative Example 1

[Production of Polyvinyl Chloride Resin Film]

Five parts by weight of polyvinyl chloride resin and 95 parts by weight of tetrahydrofuran were stirred and mixed, giving a polyvinyl chloride resin solution. The resulting polyvinyl chloride resin solution was applied by means of a doctor blade so as to give a film thickness when dry of 30 μm, then dried in vacuo at 120° C. for 2 hours to give a polyvinyl chloride resin film.

[Measurement of Relative Permittivity]

The polyvinyl chloride resin film obtained as described above was cut to a size of 4×4 cm, and the relative permittivity of the film was measured in the same way as in Example 1. The relative permittivity was 3.1.

[Production of Polymer Electrolyte Membrane]

The polyvinyl chloride resin film produced as described above was immersed for 24 hours in the ionic liquid prepared in Synthesis Example 1 and thereby impregnated with liquid electrolyte, giving a polymer electrolyte membrane.

[Measurement of Ionic Conductivity]

The ionic conductivity at 25° C. of the resulting polymer electrolyte membrane was measured in the same way as in Example 1, and found to be $9.6 \times 10^{-4}$ S/cm.

Comparative Example 2

[Production of Polymer Electrolyte Membrane]

The polyurethane resin film obtained in Example 1 was immersed for 24 hours in 1-ethyl-3-methylimidazolium tetrafluoroborate (Aldrich Chemical Co., Ltd.) and thereby impregnated with a liquid electrolyte, giving a polymer electrolyte membrane.

[Measurement of Potential Window]

The potential window of the polymer electrolyte membrane produced as described above was measured in the same way as in Example 1, and was found to have a potential window with respect to a silver/silver chloride electrode of −1.8 V to +2.7 V.

From the above, it is apparent that the polymer electrolyte membrane of Example 1 composed of the ionic liquid of Synthesis Example 1 and a polyurethane resin as the conductive polymer had a better ionic conductivity than the polymer electrolyte membrane of Comparative Example 1 composed of the ionic liquid of Synthesis Example 1 and polyvinyl chloride. Moreover, it is apparent that a polymer electrolyte membrane in which an ionic liquid according to the invention was used had a broader potential window than a polymer electrolyte membrane in which an imidazolium-based ionic liquid was used.

Example 2

Electrical Double-Layer Capacitor 1

[Production of Polarizable Electrodes]

A polarizable electrode composition in the form of a paste was prepared by stirring and mixing together 85 parts by weight of activated carbon (MSP20, produced by Kansai Coke and Chemicals Co., Ltd.), 10 parts by weight of acetylene black, 50 parts by weight of a solution of 10 parts by weight polyvinylidene fluoride dissolved in 90 parts by weight N-methyl-2-pyrrolidone, and 165 parts by weight of N-methyl-2-pyrrolidone. This polarizable electrode composition was coated onto aluminum oxide foil with a doctor blade, then dried at 80° C. for 2 hours and roll-pressed to an electrode thickness of 30 μm, thereby giving a polarizable electrode.

[Fabrication of Electrical Double-Layer Capacitor]

Two 12 mm diameter disks were cut from the polarizable electrode produced as described above. The disks were impregnated with the ionic liquid prepared in Synthesis Example 1 by 30 minutes of immersion in the liquid under a vacuum. In addition, a 13 mm diameter disk was cut from the polyurethane resin film produced in Example 1, and impregnated with liquid electrolyte by 24 hours of immersion in the ionic liquid prepared in Synthesis Example 1. The two polarizable electrodes impregnated with this liquid electrolyte were stacked together, with the ionic liquid-impregnated polyurethane resin film therebetween. The resulting assembly was sealed in an outer case, thereby giving an electrical double-layer capacitor.

[Charge/Discharge Test]

The resulting electrical double-layer capacitor was subjected to constant current charge-discharge at a cutoff voltage during charging of 2.5 V, an end-of-discharge voltage of 0 V and a current density of 1.5 mA/cm$^2$. The electrostatic capacitance per polarizable electrode, as computed from the integrated electrical energy during discharge, was 33.4 F/g.

Example 3

Electrical Double-Layer Capacitor 2

[Production of Cellulose Derivative Film]

Five parts by weight of the cellulose derivative obtained in Synthesis Example 4 and 95 parts by weight of propylene carbonate were stirred and mixed, giving a cellulose derivative solution. The resulting cellulose derivative solution was applied by means of a doctor blade so as to give a film thickness when dry of 30 μm, then dried in vacuo at 120° C. for 2 hours to form a cellulose derivative film.

[Fabrication of Electrical Double-Layer Capacitor]

Aside from using the cellulose derivative film prepared above instead of the polyurethane resin film used in Example 1, an electrical double-layer capacitor was fabricated in the same way as in Example 1.

[Charge/Discharge Test]

The resulting electrical double-layer capacitor was subjected to a charge/discharge test under the same conditions as in Example 1. The electrostatic capacitance per polarizable electrode was 32.1 F/g.

Example 4

Electrical Double-Layer Capacitor 3

[Production of Oxyalkylene-Branched Polyvinyl Alcohol Derivative Film]

Five parts by weight of the oxyalkylene-branched polyvinyl alcohol derivative obtained in Synthesis Example 5 and 95 parts by weight of propylene carbonate were stirred and mixed, giving an oxyalkylene-branched polyvinyl alcohol derivative solution. The resulting oxyalkylene-branched polyvinyl alcohol derivative solution was applied by means of a doctor blade so as to give a film thickness when dry of 30 μm, then dried in vacuo at 120° C. for 2 hours to form an oxyalkylene-branched polyvinyl alcohol derivative film.

[Fabrication of Electrical Double-Layer Capacitor]

Aside from using the oxyalkylene-branched polyvinyl alcohol derivative film prepared above instead of the polyurethane resin film used in Example 1, an electrical double-layer capacitor was fabricated in the same way as in Example 1.

[Charge/Discharge Test]

The resulting electrical double-layer capacitor was subjected to a charge/discharge test under the same conditions as in Example 1. The electrostatic capacitance per polarizable electrode was 33.0 F/g.

Example 5

Electrical Double-Layer Capacitor 4

[Production of Cyano-Substituted Monovalent Hydrocarbon Group-Bearing Polyvinyl Alcohol Derivative Film]

Five parts by weight of the cyano-substituted monovalent hydrocarbon group-bearing polyvinyl alcohol derivative obtained in Synthesis Example 6 and 95 parts by weight of propylene carbonate were stirred and mixed, giving a cyano-substituted monovalent hydrocarbon group-bearing polyvinyl alcohol derivative solution. The resulting cyano-substituted monovalent hydrocarbon group-bearing polyvinyl alcohol derivative solution was applied by means of a doctor blade so as to give a film thickness when dry of 30 μm, then dried in vacuo at 120° C. for 2 hours to form a cyano-substituted monovalent hydrocarbon group-bearing polyvinyl alcohol derivative film.

[Fabrication of Electrical Double-Layer Capacitor]

Aside from using the cyano-substituted monovalent hydrocarbon group-bearing polyvinyl alcohol derivative film prepared above instead of the polyurethane resin film used in Example 1, an electrical double-layer capacitor was fabricated in the same way as in Example 1.

[Charge/Discharge Test]

The resulting electrical double-layer capacitor was subjected to a charge/discharge test under the same conditions as in Example 1. The electrostatic capacitance per polarizable electrode was 32.4 F/g.

Example 6

Electrical Double-Layer Capacitor 6

[Preparation of Electrolyte-Forming Composition Solution]

The following dehydration-treated components were mixed in the indicated amounts: 100 parts by weight of polyethylene glycol dimethacrylate (number of oxirene units, 9), 70.15 parts by weight of methoxypolyethylene glycol monomethacrylate (number of oxirene units, 2), 8.41 parts by weight of trimethylolpropane trimethacrylate, and 178.56 parts by weight of the cyano-substituted monovalent hydrocarbon group-bearing polyvinyl alcohol derivative obtained in Synthesis Example 6. Next, 85 parts by weight of the ionic liquid prepared in Synthesis Example 1 and 0.5 part by weight of azobisisobutyronitrile were added to 14.5 parts by weight of this mixed composition, thereby giving an electrolyte-forming composition.

[Fabrication of Electrical Double-Layer Capacitor]

Two polarizable electrodes fabricated in the same way as in Example 1 were cut to a diameter of 12 mm, and a cellulose separator (TF 40-35, made by Nippon Kodoshi Corporation) was cut to a diameter of 13 mm. These were impregnated with the electrolyte-forming composition solution prepared above by 30 minutes of immersion in the solution under a vacuum. The two polarizable electrodes impregnated with the electrolyte-forming composition solution were stacked together, with the electrolyte-forming composition solution-impregnated separator therebetween. The resulting assembly was sealed in an outer case and subsequently heated at 55° C. for 2 hours and at 80° C. for 0.5 hour to effect gelation, thereby giving an electrical double-layer capacitor.

[Charge/Discharge Test]

The resulting electrical double-layer capacitor was subjected to a charge/discharge test under the same conditions as in Example 1. The electrostatic capacitance per polarizable electrode was 31.5 F/g.

Example 7

Secondary Cell 1

[Production of Positive Electrode]

Ninety-two parts by weight of $LiCoO_2$ as the positive electrode active material, 3 parts by weight of Ket enblack as the conductive material, 50 parts by weight of a solution of 10 parts by weight of polyvinylidene fluoride in 90 parts by weight of N-methyl-2-pyrrolidone, and 20 parts by weight of N-methyl-2-pyrrolidone were stirred and mixed together, giving a paste-like positive electrode composition. This positive electrode composition was applied onto aluminum foil with a doctor blade, then dried at 80° C. for 2 hours and roll-pressed to an electrode thickness of 30 μm, thereby forming a positive electrode.

[Production of Negative Electrode]

Ninety-two parts by weight of mesophase carbon microbeads (MCMB 6-28, made by Osaka Gas Chemicals Co., Ltd.) as the negative electrode active material, 80 parts by weight of a solution of 10 parts by weight of polyvinylidene fluoride in 90 parts by weight of N-methyl-2-pyrrolidone, and 40 parts by weight of N-methyl-2-pyrrolidone were stirred and mixed together, giving a paste-like negative electrode composition. This negative electrode composition was applied onto copper foil with a doctor blade, then dried at 80° C. for 2 hours and roll-pressed to an electrode thickness of 30 μm, thereby forming a negative electrode.

[Preparation of Electrolyte Solution]

An electrolyte solution was prepared by dissolving 4 parts by weight of lithium bis(trifluoromethane)imide in 96 parts by weight of the ionic liquid obtained in Synthesis Example 2.

[Fabrication of Secondary Cell]

The positive electrode and negative electrode obtained as described above were cut to respective diameters of 11 mm and 12 mm, then were impregnated with the electrolyte solution prepared above by 30 minutes of immersion in the solution under a vacuum. In addition, the polyurethane resin film produced in Example 1 was cut to a diameter of 13 mm and immersed for 24 hours in the electrolyte solution prepared as described above so as to impregnate it with the solution. The electrolyte solution-impregnated positive and negative electrodes were stacked together, with the electrolyte solution-impregnated polyurethane resin film therebetween, and the resulting assembly was sealed in an outer case to give a secondary cell.

[Charge/Discharge Test]

The secondary cell produced as described above was subjected to a charge/discharge test at a charge voltage of 4.2 mV, a discharge voltage of 2.7 V, and under a constant current at a current density of 0.03 mA/cm$^2$. The cell was found to have a capacity of 0.705 mAh and a charge-discharge efficiency in the first cycle of 73.8%.

Example 8

Secondary Cell 2

[Fabrication of Secondary Cell]

Aside from using the cellulose derivative film produced in Example 3 instead of a polyurethane resin film, a secondary cell was produced in the same way as in Example 7.

[Charge/Discharge Test]

The resulting secondary cell was subjected to a charge/discharge test under the same conditions as in Example 7. The cell capacity was 0.698 mAh and the charge-discharge efficiency in the first cycle was 73.2%.

Example 9

Secondary Cell 3

[Fabrication of Secondary Cell]

Aside from using the oxyalkylene-branched polyvinyl alcohol derivative film produced in Example 4 instead of a polyurethane resin film, a secondary cell was produced in the same way as in Example 7.

[Charge/Discharge Test]

The resulting secondary cell was subjected to a charge/discharge test under the same conditions as in Example 7. The cell capacity was 0.703 mAh and the charge-discharge efficiency in the first cycle was 73.6%.

Example 10

Secondary Cell 4

[Fabrication of Secondary Cell]

Aside from using the cyano-substituted monovalent hydrocarbon-bearing polyvinyl alcohol derivative film produced in Example 6 instead of a polyurethane resin film, a secondary cell was produced in the same way as in Example 7.

[Charge/Discharge Test]

The resulting secondary cell was subjected to a charge/discharge test under the same conditions as in Example 7. The cell capacity was 0.700 mAh and the charge-discharge efficiency in the first cycle was 73.0%.

Example 11

Secondary Cell 6

[Preparation of Electrolyte-Forming Composition Solution]

The following dehydration-treated components were mixed in the indicated amounts: 100 parts by weight of polyethylene glycol dimethacrylate (number of oxirene units, 9), 70.15 parts by weight of methoxypolyethylene glycol monomethacrylate (number of oxirene units, 2), 8.41 parts by weight of trimethyloipropane trimethacrylate, and 178.56 parts by weight of the cyano-substituted monovalent hydrocarbon group-bearing polyvinyl alcohol derivative obtained in Synthesis Example 6. Next, 85 parts by weight of the electrolyte solution prepared in Example 7 and 0.5 part by weight of azobisisobutyronitrile were added to 14.5 parts by weight of this mixed composition, giving an electrolyte composition.

[Fabrication of Secondary Cell]

A positive electrode and a negative electrode obtained in the same way as in Example 7 were cut to respective diameters of 11 mm and 12 mm, and a cellulose separator (TF 40-30, made by Nippon Kodoshi Corporation) was cut to a diameter of 13 mm. All three were impregnated with the electrolyte-forming composition solution prepared above by 30 minutes of immersion in the solution under a vacuum. The positive electrode and negative electrode impregnated with the electrolyte-forming composition solution were stacked together, with the electrolyte-forming composition solution-impregnated separator therebetween. The resulting assembly was sealed within an outer case, then heated at 55° C. for 2 hours and at 80° C. for 0.5 hour to induce gelation, thereby giving a secondary cell.

[Charge/Discharge Test]

The resulting secondary cell was subjected to a charge/discharge test under the same conditions as in Example 7. The cell had a capacity of 0.692 mAh and a charge-discharge efficiency in the first cycle of 73.1%.

Example 12

Secondary Cell 7

[Fabrication of Electrolyte Solution]

An electrolyte solution was prepared by dissolving 4 parts by weight of lithium bis(trifluoromethanesulfonyl)imide in 96 parts by weight of the ionic liquid obtained in Synthesis Example 2, then adding 10 parts by weight of vinylene carbonate.

[Production of Secondary Cell]

Aside from using the electrolyte solution prepared as described above, a secondary cell was produced in the same way as in Example 7.

[Charge/Discharge Test]

The resulting secondary cell was subjected to a charge/discharge test under the same conditions as in Example 7. The cell capacity was 0.708 mAh and the charge-discharge efficiency in the first cycle was 75.5%.

Example 13

Secondary Cell 8

[Fabrication of Secondary Cell]

The positive electrode produced in Example 7 was cut to a diameter of 11 mm, then was impregnated with the electrolyte solution prepared in Example 7 by 30 minutes of immersion in the solution under a vacuum. In addition, the polyurethane resin film produced in Example 1 was cut to a diameter of 13 mm and impregnated with the electrolyte solution prepared in Example 7 by 24 hours of immersion therein. This electrolyte solution-impregnated positive electrode and a 12 mm diameter stamped lithium metal disk were stacked together, with an electrolyte solution-impregnated polyurethane resin film in between, and the resulting assembly was sealed in an outer case to form a secondary cell.

[Charge/Discharge Test]

The resulting secondary cell was subjected to a charge/discharge test under the same conditions as in Example 7. The cell capacity was 0.695 mAh and the charge-discharge efficiency in the first cycle was 72.7%.

Example 14

Secondary Cell 9

[Fabrication of Secondary Cell]

A positive electrode produced in the same way as in Example 7 was cut to a diameter of 11 mm, and a cellulose separator (TF 40-30, made by Nippon Kodoshi Corporation) was cut to a diameter of 13 mm. These were both impregnated with an electrolyte-forming composition solution prepared in the same way as in Example 11 by 30 minutes of immersion in the solution under a vacuum. This electrolyte-forming composition solution-impregnated positive electrode and a 12 mm diameter stamped lithium metal disk were stacked together, with an electrolyte-forming composition solution-impregnated separator therebetween. The resulting assembly was sealed within an outer case, then heated at 55° C. for 2 hours and at 80° C. for 0.5 hour to induce gelation, thereby giving a secondary cell.

[Charge/Discharge Test]

The resulting secondary cell was subjected to a charge/discharge test under the same conditions as in Example 7. The cell capacity was 0.688 mAh and the charge-discharge efficiency in the first cycle was 72.2%.

The invention claimed is:

1. A nonaqueous electrolyte characterized by containing:
an ionic liquid which has general formula (1) below and is liquid at not higher than 50° C.

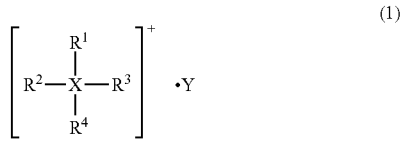

wherein $R^1$ to $R^4$ are each independently an alkyl group of 1 to 5 carbons or an alkoxyalkyl group of the formula $R'\text{—}O\text{—}(CH_2)_n\text{—}$ ($R'$ being methyl or ethyl, and the letter n being an integer from 1 to 4), and any two from among $R^1$, $R^2$, $R^3$ and $R^4$ may together form a ring, with the proviso that at least one of $R^1$ to $R^4$ is an alkoxyalkyl group of the above formula,
X is a nitrogen atom or a phosphorus atom, and
Y is a monovalent anion; and
an ion-conductive polymer having a relative permittivity at 25° C. and 1 MHz of 5 to 50.

2. A nonaqueous electrolyte which is characterized in that it is obtained by curing a composition containing:
an ionic liquid which has general formula (1) below and is liquid at not higher than 50° C.

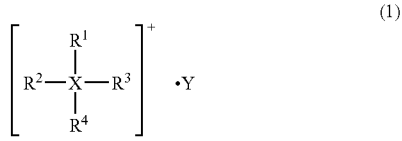

wherein $R^1$ to are each independently an alkyl group of 1 to 5 carbons or an alkoxyallcyl group of the formula $R'\text{—}O\text{—}(CH_2)_n\text{—}$ ($R^1$ being methyl or ethyl, and the letter n being an integer from 1 to 4), and any two from among $R^1$, $R^2$, $R^3$ and $R^4$ may together form a ring, with the proviso that at least one of $R^1$ to $R^4$ is an alkoxyalkyl group of the above formula,
X is a nitrogen atom or a phosphorus atom, and
Y is a monovalent anion;
a compound having a reactive double bond on the molecule; and
an ion-conductive polymer.

3. The nonaqueous electrolyte of claim 2, which is characterized in that the ion-conductive polymer has a relative permittivity at 25° C. and 1 MHz of 5 to 50.

4. The nonaqueous electrolyte of claim 1 or 2 which is characterized by containing a lithium salt.

5. The nonaqueous electrolyte of claim 4 which is characterized in that the lithium salt is $LiBF_4$, $LiPF_6$, $Li(CF_3SO_2)_2N$, $LiCF_3SO_3$ or $LiCF_3CO_2$.

6. The nonaqueous electrolyte of claim 1 or 2, which is characterized in that the ion-conductive polymer is a non-crystalline polymer.

7. The nonaqueous electrolyte of claim 1 or 2, which is characterized in that the ion-conductive polymer is a thermoplastic polyurethane resin.

8. The nonaqueous electrolyte of claim 1 or 2, which is characterized in that the ion-conductive polymer is a hydroxyalkyl polysaccharide or a hydroxyalkyl polysaccharide derivative.

9. The nonaqueous electrolyte of claim 1 or 2, which is characterized in that the ion-conductive polymer is a polymeric compound having an average degree of polymerization of at least 20 and containing polyvinyl alcohol groups of general formula (2) below

wherein n is a number from 20 to 10,000, some or all of the hydroxyl groups on the polyvinyl alcohol units being substituted with oxyalkylene-bearing units having an average molar substitution of at least 0.3.

10. The nonaqueous electrolyte of claim 1 or 2, which is characterized in that the ion-conductive polymer is a polymeric compound having an average degree of polymerization of at least 20 and containing polyvinyl alcohol units of general formula (2) below

wherein n is a number from 20 to 10,000, some or all of the hydroxyl groups on the polyvinyl alcohol units being substituted with cyano-substituted monovalent hydrocarbon groups.

11. The nonaqueous electrolyte of claim 1 or 2, which is characterized in that the ion-conductive polymer is a polymeric compound having units of formula (3) and units of formula (4)

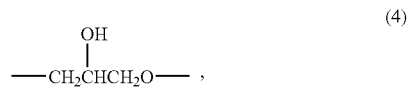

wherein at least 10% of the end groups on the molecular chain are capped with one or more groups selected from among halogen atoms, substituted or unsubstituted monovalent hydrocarbon groups, $R^5CO\text{—}$ groups ($R^5$ being a substituted or unsubstituted monovalent hydrocarbon group), $R^5_3Si\text{—}$ groups ($R^5$ being the same as above), amino groups, alkylamino groups, $H(OR^6)_m\text{—}$ groups ($R^6$ being an alkylene group of 2 to 4 carbons, and m being an integer from 1 to 100) and phosphorus atom-containing groups.

12. The nonaqueous electrolyte of claim 1 or 2, which is characterized in that the ionic liquid is liquid at not higher than 25° C.

13. The nonaqueous electrolyte of claim 1 or 2, which is characterized in that X is a nitrogen atom, R' is methyl, and n is 2.

14. The nonaqueous electrolyte of claim 1 or 2, which is characterized in that the ionic liquid has general formula (5) below

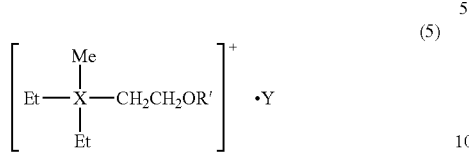
(5)

wherein R' is methyl or ethyl, X is a nitrogen atom or a phosphorus atom, Y is a monovalent anion, Me stands for methyl and Et stands for ethyl.

15. The nonaqueous electrolyte of claim 1 or 2, which is characterized in that Y is $BF_4^-$, $PF_6^-$, $(CF_3SO_2)_2N^-$, $CF_3SO_3^-$ or $CF_3CO_2^-$.

16. An electrical double-layer capacitor comprising a pair of polarizable electrodes, a separator between the polarizable electrodes and a nonaqueous electrolyte, which electrical double-layer capacitor is characterized in that the nonaqueous electrolyte is a nonaqueous electrolyte according to claim 1 or 2.

17. A nonaqueous electrolyte secondary cell comprising a positive electrode which contains a lithium-containing double oxide, a negative electrode which contains a carbonaceous material capable of lithium ion insertion and extraction or contains metallic lithium, a separator between the positive and negative electrodes, and a nonaqueous electrolyte;

which nonaqueous secondary cell is characterized in that the nonaqueous electrolyte is a nonaqueous electrolyte according to claim 1 or 2.

\* \* \* \* \*